(12) United States Patent
Yamamizu et al.

(10) Patent No.: US 7,755,359 B2
(45) Date of Patent: *Jul. 13, 2010

(54) MAGNETIC RESONANCE IMAGING APPARATUS WITH NOISE SUPPRESSING STRUCTURE

(75) Inventors: Takashi Yamamizu, Adachi-ku (JP); Shichihei Sakuragi, Kashiwa (JP); Hirotaka Takeshima, Ryugasaki (JP); Hiroyuki Takeuchi, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 151 days.

This patent is subject to a terminal disclaimer.

(21) Appl. No.: 11/628,097

(22) PCT Filed: May 25, 2005

(86) PCT No.: PCT/JP2005/009523

§ 371 (c)(1),
(2), (4) Date: Jan. 17, 2008

(87) PCT Pub. No.: WO2005/115239

PCT Pub. Date: Dec. 8, 2005

(65) Prior Publication Data

US 2008/0309343 A1    Dec. 18, 2008

(30) Foreign Application Priority Data

May 31, 2004  (JP)  .............................. 2004-160779
Mar. 14, 2005  (JP)  .............................. 2005-070214

(51) Int. Cl.
*G01V 3/00*    (2006.01)

(52) U.S. Cl. .................................................... 324/320

(58) Field of Classification Search ......... 324/300–322; 600/410–435
See application file for complete search history.

(56) References Cited

U.S. PATENT DOCUMENTS

| | | | | |
|---|---|---|---|---|
| 5,630,415 A * | 5/1997 | Kaufman | ..................... | 600/422 |
| 5,786,695 A * | 7/1998 | Amor et al. | .................. | 324/320 |
| 6,208,141 B1 * | 3/2001 | Amor et al. | .................. | 324/318 |
| 6,326,788 B1 * | 12/2001 | Mulder et al. | ............... | 324/318 |
| 6,437,568 B1 * | 8/2002 | Edelstein et al. | ............ | 324/318 |
| 6,642,717 B2 * | 11/2003 | Dietz et al. | .................. | 324/318 |
| 6,765,382 B2 * | 7/2004 | Dewdney | ..................... | 324/320 |
| 6,894,497 B2 * | 5/2005 | Renz | ............................ | 324/318 |
| 6,933,722 B2 * | 8/2005 | Tsuda et al. | ................. | 324/318 |
| 6,954,068 B1 * | 10/2005 | Takamori et al. | ............ | 324/318 |
| 6,984,982 B2 * | 1/2006 | Huang et al. | ................. | 324/318 |
| 7,034,537 B2 * | 4/2006 | Tsuda et al. | ................. | 324/320 |
| 7,307,421 B2 * | 12/2007 | Kurome et al. | .............. | 324/318 |
| 7,375,518 B2 * | 5/2008 | Kurome et al. | .............. | 324/307 |

(Continued)

FOREIGN PATENT DOCUMENTS

JP    4-250136    9/1992

(Continued)

*Primary Examiner*—Brij B Shrivastav
*Assistant Examiner*—Dixomara Vargas
(74) *Attorney, Agent, or Firm*—Cooper & Dunham LLP

(57) ABSTRACT

A magnetic resonance imaging apparatus capable of suppressing noise caused by vibration of a gradient magnetic field coil and improving image quality includes a large number of ferromagnetic shims disposed in a large number of holes formed in a shim tray, and vibration dampers disposed in holes formed in the shim tray to reduce noise generated by vibration of a gradient magnetic field generating coil.

15 Claims, 12 Drawing Sheets

U.S. PATENT DOCUMENTS

| | | |
|---|---|---|
| 7,541,812 B2 * | 6/2009 | Nogami .................. 324/319 |
| 2003/0011456 A1 | 1/2003 | Yoshida et al. |
| 2008/0191698 A1 * | 8/2008 | Nogami .................. 324/318 |
| 2008/0211504 A1 * | 9/2008 | Kurome et al. ............ 324/320 |

FOREIGN PATENT DOCUMENTS

| | | |
|---|---|---|
| JP | 8-154918 | 6/1996 |
| JP | 10-201735 | 8/1998 |
| JP | 11-137535 | 5/1999 |
| JP | 2000-126152 | 5/2000 |
| JP | 3156088 | 2/2001 |
| JP | 2002-17705 | 1/2002 |
| JP | 2002-360537 | 12/2002 |

* cited by examiner

MAGNETIC RESONANCE IMAGING APPARATUS WITH NOISE SUPPRESSING STRUCTURE

TECHNICAL FIELD

The present invention relates to a magnetic resonance imaging apparatus, and more particularly to a magnetic resonance imaging apparatus capable of suppressing noise generated with vibration of a gradient magnetic field coil when the coil being energized.

BACKGROUND ART

In a magnetic resonance imaging apparatus (hereinafter referred to as an "MRI apparatus"), an object to be examined as a target to be examined is placed within a uniform static magnetic field, and a nuclear magnetic resonance signal (hereinafter referred to as an "NMR signal") from the object to be examined is detected by utilizing a nuclear magnetic resonance phenomenon that is caused by nuclei of atoms making up a body of the object to be examined when an electromagnetic wave is irradiated to the object to be examined. By reconstructing an image from the detected NMR signal, a magnetic resonance image (hereinafter referred to as an "MRI image") representing physical properties of the object to be examined is obtained. To provide position information in such an imaging process, a gradient magnetic field is applied in superimposed relation to the static magnetic field.

In a vertical magnetic field system in which the direction of the static magnetic field is orthogonal to the direction of a body axis of the object to be examined, a pair of gradient magnetic field coils are arranged in vertically opposed relation inside a pair of static magnetic field generating sources (i.e., within a uniform static magnetic field) which are also arranged in vertically opposed relation. Further, because the gradient magnetic field is generated in each of three-axis directions orthogonal to each other, the pair of gradient magnetic field coils are each constituted by three sets of pair of magnetic field generating coils.

A gradient magnetic field power supply is connected to each gradient magnetic field coil such that a pulse-like current is applied to the gradient magnetic field coil at the proper timing and voltage depending on conditions which are required when imaging and examination are carried out in the MRI apparatus. However, when the pulse-like current is applied to the gradient magnetic field coil, the gradient magnetic field coil is vibrated by the action of the Lorentz's force, thus producing noise.

As the prior art for solving that problem, there is known an MRI apparatus having a structure in which the gradient magnetic field coil is put in a recess formed in a pole piece for sound insulation (see Patent Document 1).

In the prior art disclosed in Patent Document 1, the gradient magnetic field coil is attached to the pole piece while a D-piece made of a soft material, e.g., rubber, is interposed between them, whereby the vibration of the gradient magnetic field coil is prevented from being transferred to the pole piece.

In the above-cited Patent Document 1, however, if the D-piece is too soft, a problem arises in that a position variation caused by the vibration of the gradient magnetic field coil is increased and fluctuation of the gradient magnetic field caused by the increased position variation brings about an image artifact.

To solve such a problem, Patent Document 2 discloses a technique of distributing a load imposed on the gradient magnetic field coil to a large number of elastic bodies so that a displacement of each elastic body is reduced to a sufficiently small amount, thereby suppressing fluctuation in distribution of the gradient magnetic field.

Patent Document 3 also discloses a technique for preventing noise caused by the vibration of the gradient magnetic field coil.

In Patent Document 3, the noise is reduced by setting a spectrum characteristic of the waveform of a current applied to the gradient magnetic field coil so that the intensity of a component having a frequency f matched with the natural frequency of the gradient magnetic field coil including a holding member is substantially 0.

Further, Patent Document 3 discloses a method for modifying parameters related to the natural frequency, such as an axial length and a fixed position of the holding member, so that in a certain particular spectrum component, a frequency at which the intensity is substantially 0 is matched with the natural frequency of the gradient magnetic field coil.

Meanwhile, Patent Document 4 discloses an MRI apparatus in which a ferromagnetic shim is arranged between a static magnetic field generating source and the gradient magnetic field coil to increase uniformity of the static magnetic field, thereby improving image quality.

Patent Document 1: JP,A 11-137535
Patent Document 2: Japanese Patent 3156088
Patent Document 3: JP,A 10-201735
Patent Document 4: JP,A 2002-360537

However, the technique disclosed in Patent Document 2 has the problems as follows. In order to reduce the displacement of each elastic body to the sufficiently small amount, a large number of elastic bodies have to be arranged over a wide area. Therefore, although the noise caused by the vibration of the gradient magnetic field coil can be suppressed, a difficulty occurs in improving image quality because an area for arrangement of image quality improving means, such as disclosed in Patent Document 4, is limited.

Also, the technique disclosed in Patent Document 3 has the problems as follows.

In the MRI apparatus, imaging is required to be performed by applying the gradient magnetic field that has various frequency components ranging from a normal sequence to a high-speed sequence. Therefore, the imaging performed using only the particular current waveform, which has been adjusted so as to suppress the vibration, is not adaptable for various sequences.

Further, the technique of modifying the parameters of the holding member also has a difficulty in preventing noise and improving image quality because it is practically impossible to modify the parameters, such as the axial length and the fixed position of the holding member, for each of the various sequences.

In an aspect of this disclosure, there is provided a magnetic resonance imaging apparatus which can suppress noise caused by vibration of a gradient magnetic field coil and can improve image quality.

In another aspect of this disclosure, there is provided a magnetic resonance imaging apparatus comprising static magnetic field generating means for generating a static magnetic field in an imaging space, gradient magnetic field generating means for generating a gradient magnetic field in the imaging space, RF magnetic field generating means for generating an RF magnetic field, signal receiving means for detecting a nuclear magnetic resonance signal, and signal processing means for reconstructing an image by using the detected nuclear magnetic resonance signal.

In addition to the above-mentioned components, the magnetic resonance imaging apparatus further comprises static magnetic-field non-uniformity correcting means disposed between the static magnetic field generating means and the gradient magnetic field generating means, including a plurality of static magnetic-field non-uniformity correcting members, and having a plurality of holes formed therein; and a plurality of vibration isolating members disposed in the plurality of holes formed in the static magnetic-field non-uniformity correcting means and suppressing transfer of vibration generated in the gradient magnetic field generating means to the static magnetic field generating means.

In another aspect of this disclosure, there is provided a magnetic resonance imaging apparatus comprising static magnetic field generating means for generating a static magnetic field in an imaging space, gradient magnetic field generating means for generating a gradient magnetic field in the imaging space, RF magnetic field generating means for generating an RF magnetic field, signal receiving means for detecting a nuclear magnetic resonance signal, and control means for reconstructing an image by using the detected nuclear magnetic resonance signal and for generating the gradient magnetic field and the RF magnetic field in accordance with a plurality of pulse sequences.

In addition to the above-mentioned components, the magnetic resonance imaging apparatus further comprises vibration suppressing means for modifying a frequency characteristic or a transfer characteristic of vibration caused when the gradient magnetic field generating means is vibrated.

The configuration of the above-mentioned magnetic resonance imagine apparatus makes it possible to secure areas for arrangement of two means, i.e., the static magnetic-field non-uniformity correcting means and the vibration suppressing means, to reduce noise caused by the vibration of the gradient magnetic field generating means, and to suppress deterioration of image quality.

In addition, such magnetic resonance imaging apparatus makes it possible to suppress generation of the noise caused by the vibration of the gradient magnetic field coil in a manner adapted for each of various sequences, and to improve image quality.

REFERENCE NUMERALS

1 . . . central processing unit, 2 . . . sequencer, 3 . . . transmission system, 4 . . . static magnetic field generating magnet, 5 . . . reception system, 7 . . . patient as target to be examined, 8 . . . RF oscillator, 9 . . . modulator, 10 . . . RF amplifier, 11 . . . irradiation coil, 12 . . . gradient magnetic field power supply, 13 . . . gradient magnetic field coil, 14 . . . reception coil, 15 . . . amplifier, 16 . . . orthogonal phase detector, 17 . . . ADC, 18 . . . display, 19 . . . optical disc, 20 . . . magnetic disc, 22 . . . shim tray, 23 . . . vibration damper, 24 . . . screw hole, 31 . . . gantry, 32 . . . table, 33 . . . processor, 34 . . . monitor, 40 . . . RF coil fixture, 41 . . . gradient magnetic field coil fixture, and 42 . . . actuator.

BEST MODE FOR CARRYING OUT THE INVENTION

A system configuration of a general MRI apparatus will be described in detail below with reference to FIG. 1.

Figure 1:
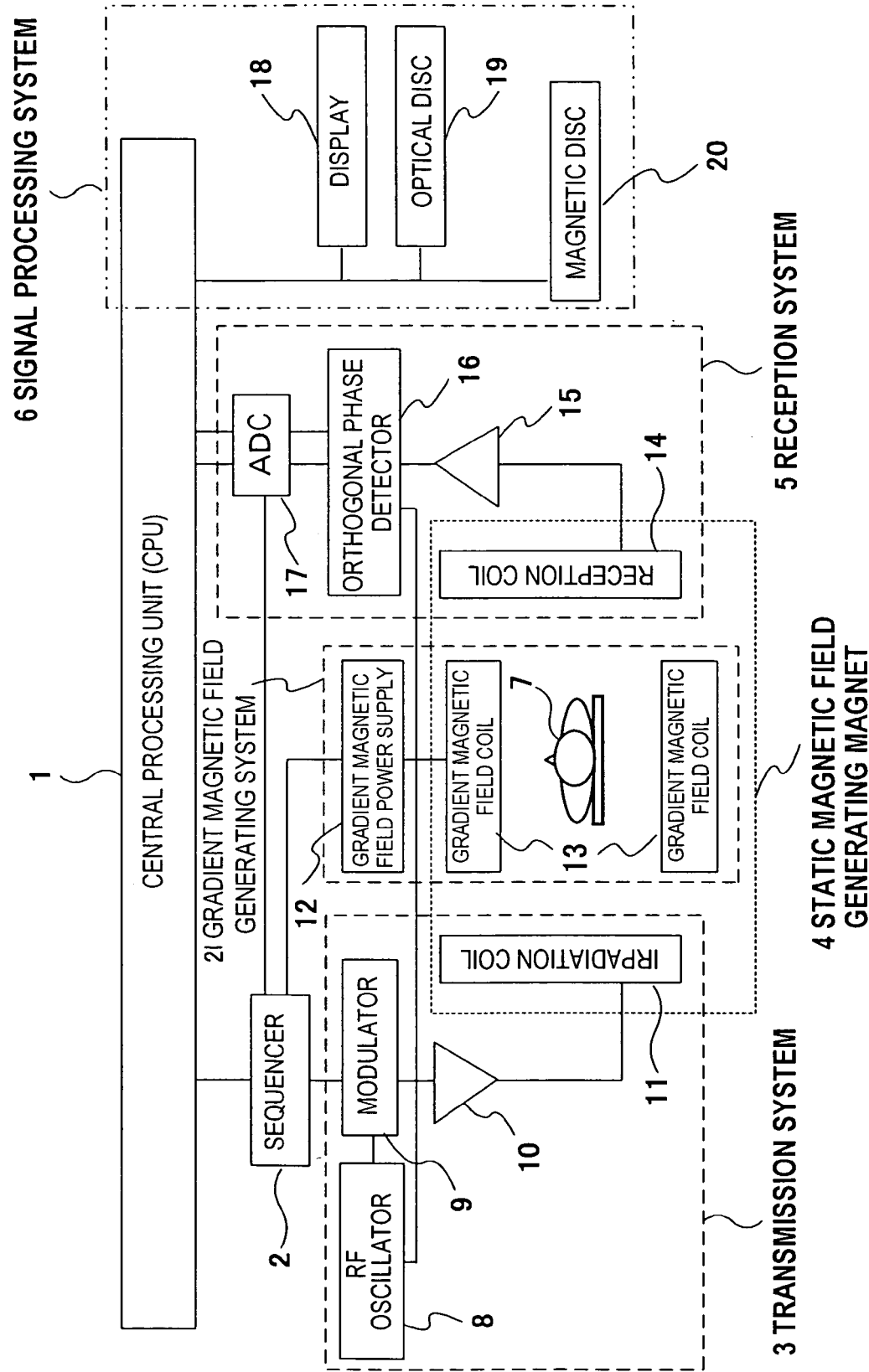
FIG. 1 is a block diagram of an MRI apparatus to which is applied the present invention.

In FIG. 1, the MRI apparatus comprises mainly a central processing unit (hereinafter abbreviated to a "CPU") 1, a sequencer 2, a transmission system 3, a static magnetic field generating magnet 4, a reception system 5, a gradient magnetic field generating system 21, and a signal processing system 6.

The CPU 1 controls the sequencer 2, the transmission system 3, the reception system 5, and the signal processing system 6 in accordance with a predetermined program. The sequencer 2 is operated in accordance with control commands from the CPU 1 and sends various instructions, which are required for collecting image data of a slice plane for tomography of a patient 7 as a target to be examined, to each of the transmission system 3, the gradient magnetic field generating system 21, and the reception system 5.

The transmission system 3 includes an RF oscillator 8, a modulator 9, and an irradiation coil 11. A reference RF pulse from the RF oscillator 8 is subjected to amplitude modulation by the modulator 9 in accordance with a command from the sequencer 2. The RF pulse thus subjected to the amplitude modulation is amplified by an RF amplifier 10 and supplied to the irradiation coil 11, whereby a predetermined pulse-like electromagnetic wave is irradiated to the object to be examined.

The static magnetic field generating magnet 4 is to generate a uniform static magnetic field around the object to be examined 7 in a predetermined direction. The irradiation coil 11, a gradient magnetic field coil 13, and a reception coil 14 are arranged within the static magnetic field generating magnet 4.

The gradient magnetic field coil 13 is included in the gradient magnetic field generating system 21 and is supplied with a current from a gradient magnetic field power supply 12 to generate a gradient magnetic field under control of the sequencer 2.

The reception system 5 is to detect an RF signal (NMR signal) released from the body tissue of the object to be examined 7 based on the nuclear magnetic resonance of atomic nuclei, and it includes the reception coil 14, an amplifier 15, an orthogonal phase detector 16, and an A/D converter 17. The RF signal (NMR signal) responsively obtained from the object to be examined 7 upon irradiation of the electromagnetic wave from the irradiation coil 14 is detected by the reception coil 14 disposed near the object to be examined 7 and is inputted to the A/D converter 17 through the amplifier 15 and the orthogonal phase detector 16. The NMR signal is converted to a digital signal by the A/D converter 17, and the digital signal is sent to the CPU 1.

The signal processing system 6 includes an external storage, such as a magnetic disc 20 and an optical disc 19, and a display 18 constituted by, e.g., a CRT. When data from the reception system 5 is inputted to the CPU 1, the CPU 1 executes necessary processes, such as signal processing and image reconstruction, to display an image in the desired slice plane for tomography of the object to be examined 7 on the display 18 and to store the image in the external storage, e.g., the magnetic disc 20.

Figure 2:
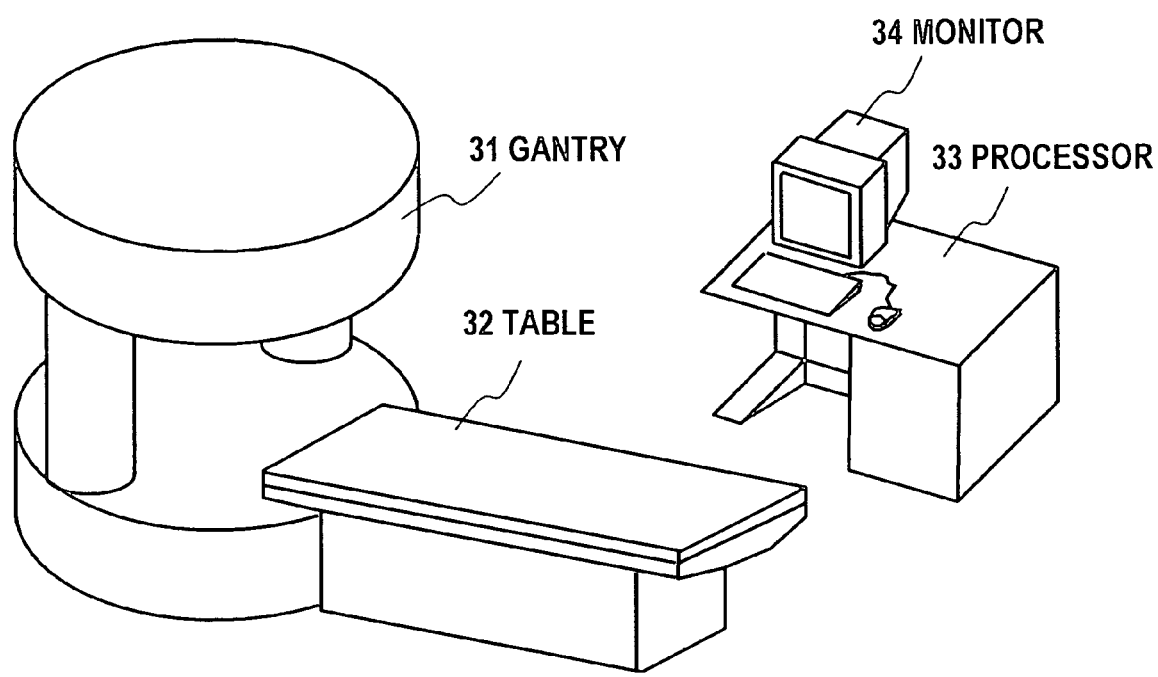
FIG. 2 is a schematic perspective view of the MRI apparatus to which is applied the present invention.

FIG. 2 is a schematic perspective view of an open-type MRI apparatus to which is applied the present invention. Herein, the open-type MRI apparatus means an MRI apparatus in which static magnetic field generating magnets are oppositely arranged, for example, at positions spaced vertically or laterally (not shown in FIG. 2) with an imaging space defined between the magnets, and an MRI image of the object to be examined placed in the imaging space is obtained while a static magnetic field is formed perpendicularly to the opposed surfaces of the static magnetic field generating magnets.

In FIG. 2, the MRI apparatus comprises, for example, a gantry 31 which includes the static magnetic field generating magnets to generate the static magnetic field, the reception coil to receive the NMR signal, etc. and which accommodates the object to be examined therein, a table 32 on which the object to be examined is placed, a processor 33 which executes arithmetic and logical operations for reconstructing an image in accordance with the NMR signal obtained from the reception coil inside the gantry 31 and produces an MRI image, and a monitor 34 which is disposed on the processor 33 and displays the MRI image produced by the processor 33.

Note that, in FIG. 2, a cable connecting the gantry 31 and the processor 33 for sending the NMR signal obtained from the reception coil to the processor 33 is omitted.

The gantry 31 will be described below with reference to FIG. 3.

Figure 3:
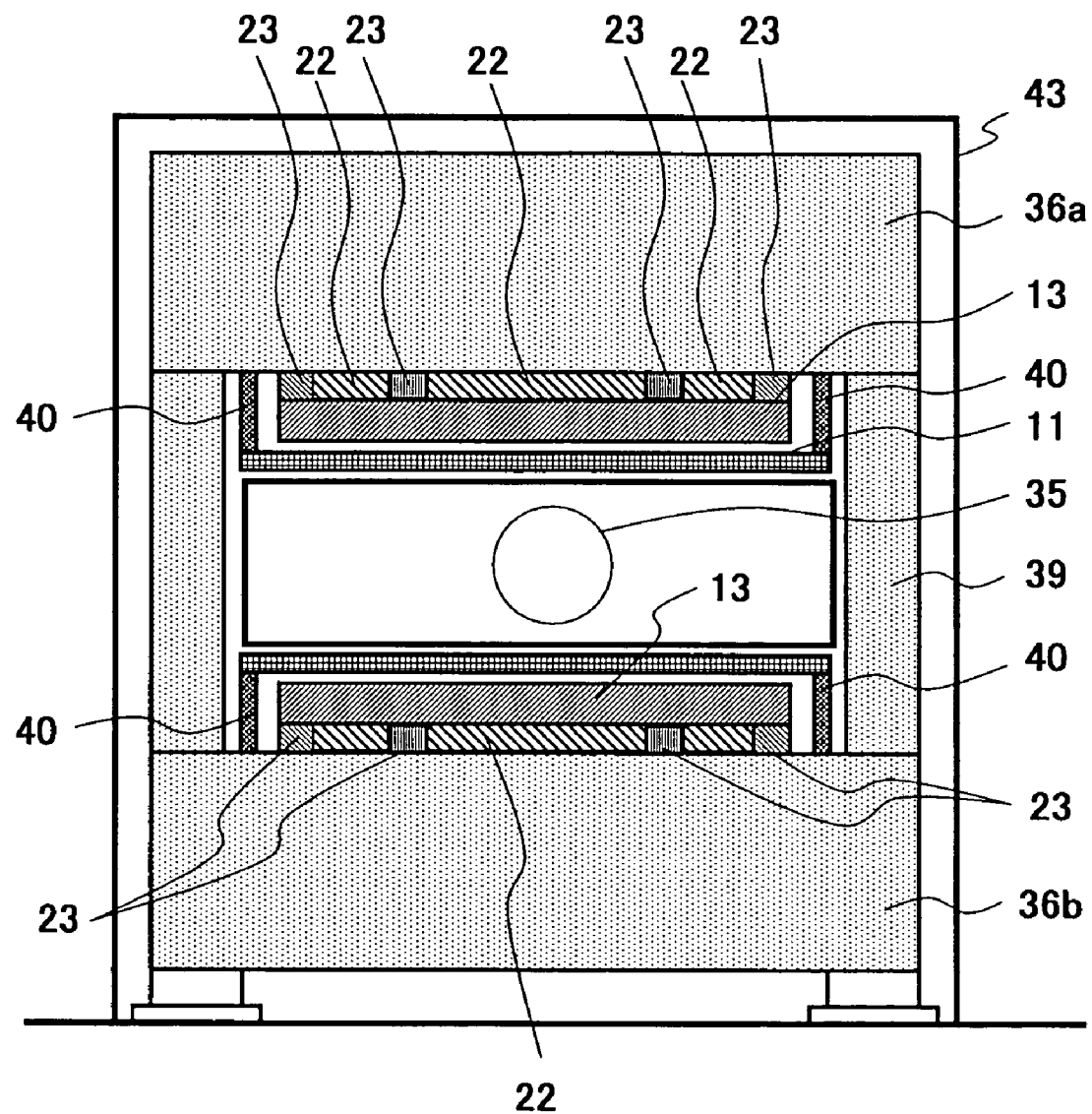
FIG. 3 is a schematic sectional view of an MRI apparatus according to a first embodiment of the present invention.

FIG. 3 shows the case of employing, as in FIG. 2, an open-type superconducting magnet 4 which generates a static magnetic field in a central area by static magnetic field generating sources arranged in vertically opposed relation. In FIG. 3, reference numeral 35 denotes a uniform magnetic field space, 36a and 36b denote respectively an upper cryostat and a lower cryostat each of which accommodates a superconducting coil, and 13 denotes a gradient magnetic field coil for generating a gradient magnetic field in the uniform magnetic space 36. Further, reference numeral 39 denotes a connecting pipe for connecting the upper cryostat 36a and the lower cryostat 36b to each other, 40 denotes an RF coil fixture for fixing the RF coil 11 to corresponding one of the upper cryostat 36a and the lower cryostat 36b, and 43 denotes a cover.

In addition, reference numeral 22 denotes a shim tray for arranging a large number of ferromagnetic shims (iron shims) respectively in a large number of holes (screw holes). The shim 22 is disposed between the static magnetic field generating magnet 4 and the gradient magnetic field coil 13. Reference numeral 23 denotes a vibration damper which is disposed within a hole formed in the shim tray 22 and is made of rubber, resin or the like, for example, to reduce noise generated when vibration of the gradient magnetic field coil 13 is propagated to the static magnetic field generating magnet through solid bodies and the static magnetic field generating magnet, etc. are vibrated correspondingly.

Here, a vibration transfer rate representing the performance of the vibration damper 23 is generally defined by the following formula (1) depending on values of the spring constant of the vibration damper 23 and the natural frequency of a system decided by a support load:

[Formula 1]

$$T_r = \left| \left\{ 1 - \left( \frac{f}{f_n} \right)^2 \right\}^{-1} \right|$$

$$= \left| \left\{ 1 - \left( \frac{f}{\frac{1}{2\pi}\sqrt{\frac{K}{m}}} \right)^2 \right\}^{-1} \right| \quad (1)$$

In the formula (1), Tr is the vibration transfer rate, fn is the natural vibration frequency of the system, f is the vibration frequency, K is the spring constant, and m is the support load.

As seen from the above formula (1), a vibration frequency component of 400 Hz or above can be suppressed at a vibration transfer rate of 1/10 or less by optimizing the spring constant of the vibration damper 23 so that the natural vibration frequency of the system is about 120 Hz, for example.

Conversely, the above point is equivalent to that an upper limit value of the spring constant is decided by setting a minimum frequency of the vibration to be isolated.

Looking from the viewpoint of noise, the human ear's sensibility derived from an equi-loudness curve is maximum for sounds in the range of 3 kHz to 5 kHz and is gradually reduced for sounds at other frequencies than that range.

Thus, sound noise in the range of about 3 kHz to 5 kHz for which the human ear's sensibility is high can be sufficiently reduced by setting the lowest frequency of the vibration to be isolated to 3 kHz, determining the spring constant K at which the vibration transfer rate is sufficiently reduced (for example, to 1/10 or less) when the frequency is 3 kHz, and employing the determined value as the upper limit value of the spring constant.

The upper limit value of the spring constant can be determined by using the above-described method. Basically, however, higher vibration isolation performance is obtained by setting the vibration isolation frequency set to a lower value and setting the spring constant to a value as small as possible.

On the other hand, if the spring constant is set to be too small, the amplitude of the vibration of the gradient magnetic field coil 13 itself is increased to such an extent as distorting the gradient magnetic field which is applied from the gradient magnetic field coil 13 to give position information for the object to be examined.

Such a distortion of the gradient magnetic field deteriorates quality of the image captured by the MRI apparatus, and therefore the vibration of the gradient magnetic field coil 13 itself must be suppressed to be small. In particular, because the frequency characteristic of an electromagnetic force acting on the gradient magnetic field coil 13 is changed in various ways depending on the imaging sequence, to which level reaches the amplitude of the vibration at the resonance point (frequency at which the vibration transfer rate is maximized (i.e., the natural vibration frequency)) of the vibration damper 23 must also be taken into consideration.

Here, the amplitude of the vibration at the resonance point is generally defined by the following formula (2):

[Formula 2]

$$F=QKX \quad (2)$$

In the formula 2, F is the electromagnetic force loaded on the gradient magnetic field coil, Q is the resonance factor representing a ratio of the amplitude of the vibration at the resonance point to the displacement when the loaded electromagnetic force is static, K is the spring constant, and X is the amplitude of the vibration.

As seen from the above formula (2), a lower limit value of the spring constant can be decided by setting the amplitude of the vibration allowable for the gradient magnetic field coil 13.

The amplitude of the vibration allowable for the gradient magnetic field coil 13 is substantially the same value, e.g., about ±0.1 mm, in any directions. Therefore, the lower limit value of the spring constant can be decided by putting such a value in the formula (2).

The spring constant of the vibration damper 23 in the first embodiment of the present invention is set to a value between the upper limit value and the lower limit value of the spring constant, which are calculated as described above. By so setting, the vibration isolation can be achieved and the noise can be reduced, thus realizing an MRI apparatus capable of reducing deterioration in quality of the captured image, which is caused by the vibration of the gradient magnetic field coil 13.

Stated another way, according to the first embodiment of the present invention, the large number of holes are formed in the shim tray 22 for improving the uniformity of the static magnetic field, the vibration dampers 23 each having the proper spring constant are arranged in the large number of holes, and the shim tray is disposed between the gradient magnetic field coil 13 and each of the upper and lower cryostats 36a, 36b constituting the static magnetic field generating magnets. It is therefore possible to secure areas for arrangement of two means, i.e., static magnetic-field non-uniformity correcting means and vibration suppressing means, to reduce noise caused by the vibration of the gradient magnetic field coil 13, and to reduce deterioration of image quality.

Figure 4:
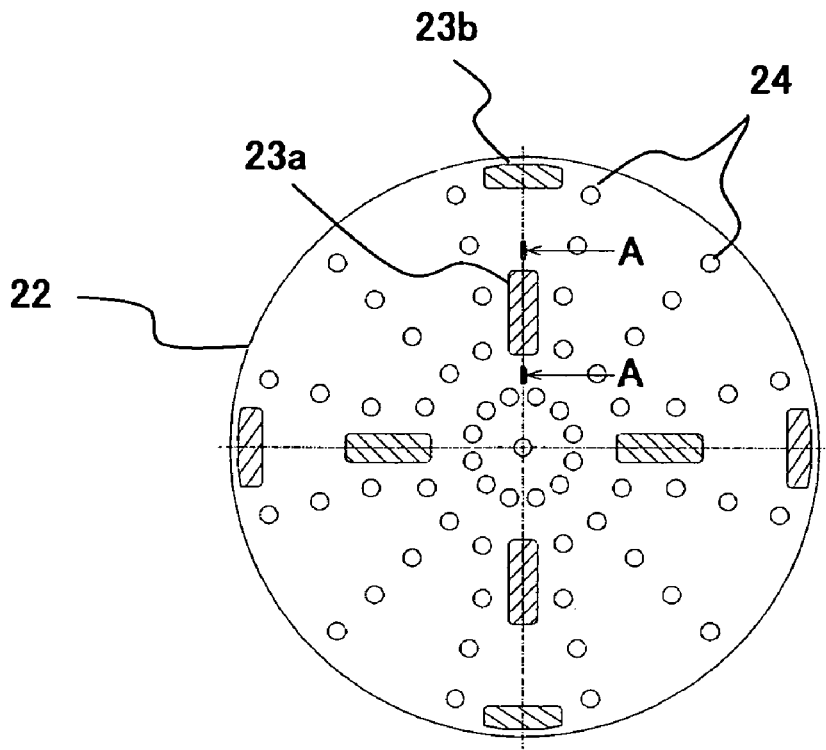
FIG. 4 is a plan view, looking from the direction of a static magnetic field, of only a shim tray and vibration dampers in an MRI apparatus according to a second embodiment of the present invention.

FIG. 4 is a plan view, looking from the direction of the static magnetic field, of only the shim tray 22 and the vibration dampers 23 in the MRI apparatus according to a second embodiment of the present invention. As in the first embodiment, this second embodiment also represents an example of an MRI apparatus employing a vertical magnetic field system in which the direction of the static magnetic field is perpendicular to the direction of the body axis of the object to be examined. Thus, an overall configuration, etc. of the MRI apparatus are common to those in the first embodiment, and therefore they are not shown.

In FIG. 4, reference numerals 23a and 23b denote vibration dampers inserted in holes which are formed in inner and outer areas positioned respectively nearer to and further away from the center of the shim tray 22, and 24 denotes a hole for arrangement of the ferromagnetic shim (iron shim) which is attached to each of the plurality of screw holes formed in the shim tray 22. The shim holes 24 are arrayed at particular intervals in the radial direction of the shim tray 22 looking from the center thereof and are also arrayed at constant intervals in the angular direction. Accordingly, calculations for deciding positions at which the ferromagnetic members are to be attached can be relatively easily performed in a step of adjusting the magnetic field.

Figure 5:
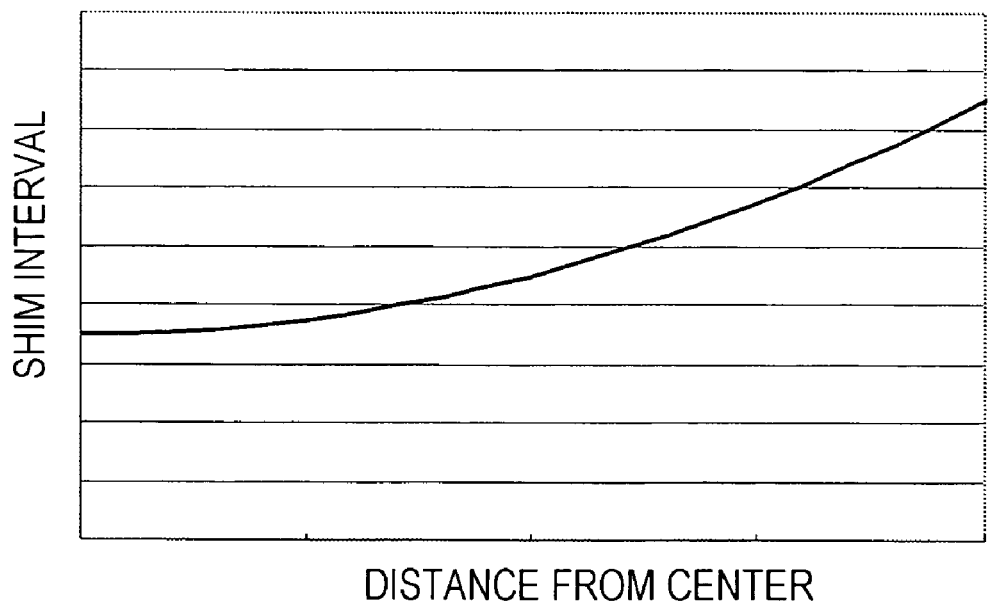
FIG. 5 is a graph showing the relationship between a shim-to-shim distance and a distance from the center of a shim tray in the case of trying to adjust the static magnetic field at predetermined uniformity.

FIG. 5 is a graph showing at what density, i.e., at what shim interval, the ferromagnetic shims (iron shims) have to be set when the static magnetic field is adjusted at predetermined uniformity. In FIG. 5, the horizontal axis represents a distance from the center of the shim tray 22, and the vertical axis represents the interval at which the ferromagnetic shims (iron shims) are arranged (i.e., a reciprocal of the number of the shims which can be arranged at the unit of area).

Because an influence upon a distribution of the magnetic field is larger in an area nearer to the center of the shim tray 22, the ferromagnetic shims (iron shims) have to be arranged at a finer density in the area nearer to the center of the shim tray 22. In other words, the interval between the holes 24 for the ferromagnetic shims (iron shims) have to be set to a smaller value in the area nearer to the center.

In the arrangement of the shim holes 24 shown in FIG. 4, therefore, the interval between one shim hole 24 and another adjacent shim hole 24 is set to a smaller value in the area nearer to the center than an area nearer to the outer periphery of the shim tray 22. Conversely speaking, the interval between the shim holes 24 is set to a larger value in the area nearer to the outer periphery than the area nearer to the center of the shim tray 22.

Corresponding to the difference in the interval of the shim holes 24 between the inner side and the outer side, the vibration dampers 23 inserted in the holes formed in the shim tray 22 comprise two kinds of eight dampers, i.e., four inner dampers 23a (first vibration isolating members) and four outer dampers 23b (second vibration isolating members). Each of the inner dampers 23a has a circumferential length smaller than a radial length such that a larger space is left to allow the arrangement of the ferromagnetic shims (iron shims) at a finer density. The four outer dampers 23b can be arranged in relatively free design because the interval between the shim holes 24 is larger than that in the inner side. In the case of FIG. 4, each of the outer dampers 23b has a circumferential width larger than a radial length.

Further, the arrangement of the vibration dampers 23a shown in FIG. 4 is rotationally symmetric about to the center of the shim tray 22, and the plurality (four in this embodiment) of vibration dampers 23a arranged at a predetermined angle (90 degrees in this embodiment) have their spring constants equal to each other. Also, the plurality (four in this embodiment) of outer vibration dampers 23b arranged at a predetermined angle (90 degrees in this embodiment) have their spring constants equal to each other. Preferably, all the spring constants of the inner and outer vibration dampers 23a, 23b are equal to each other.

With that arrangement, since the weight of the gradient magnetic field coil 13 is evenly borne at the respective positions, all the vibration dampers 23 are able to exhibit the same vibration isolation performance.

Thus, the second embodiment of the present invention can also provide similar advantages to those in the first embodiment. In addition, according to the second embodiment, since the shims are arranged in accordance with the density of the shim arrangement required for adjusting the static magnetic field at the predetermined uniformity and the vibration dampers are arranged depending on the shim-to-shim interval, proper coordination of the static magnetic field uniformalizing means and the vibration isolating means can be realized.

Figure 6:
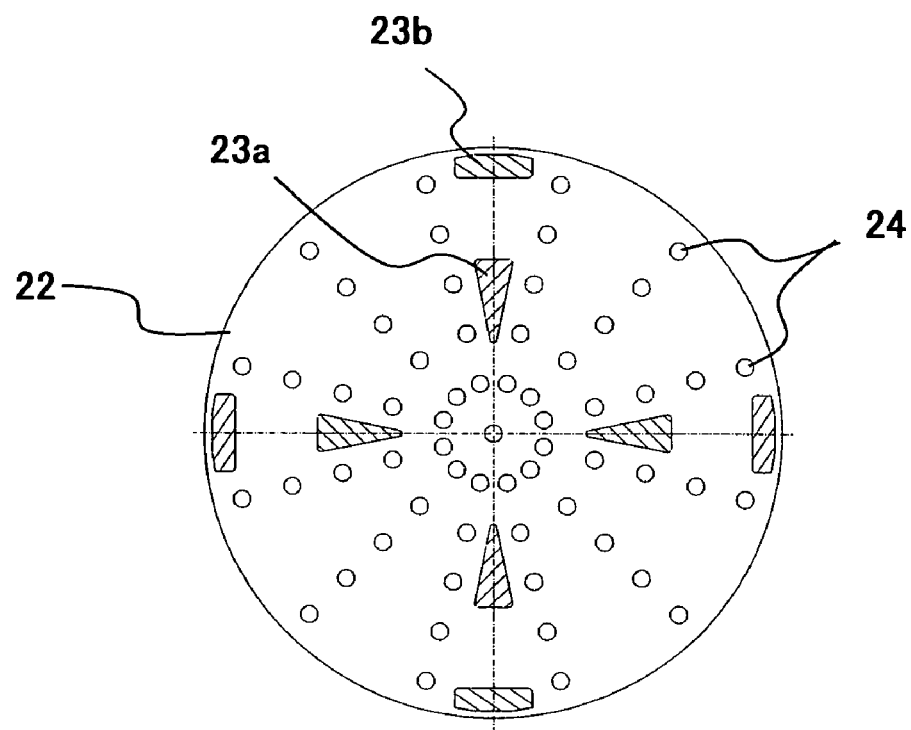
FIG. 6 is a plan view, looking from the direction of the static magnetic field, of only a shim tray and vibration dampers in an MRI apparatus according to a third embodiment of the present invention.

FIG. 6 is a plan view, looking from the direction of the static magnetic field, of only the shim tray 22 and the vibration dampers 23 in an MRI apparatus according to a third embodiment of the present invention. In comparison with the second embodiment, this third embodiment differs in that the inner vibration dampers 23a are each shaped to have a circumferential length gradually decreasing toward the center of the shim tray 22.

With such an arrangement, in addition to similar advantages to those in the second embodiment, the third embodiment can provide the advantage that a larger space for arrangement of the ferromagnetic shims (iron shims) can be ensured near the center of the shim tray 22.

Figure 7:
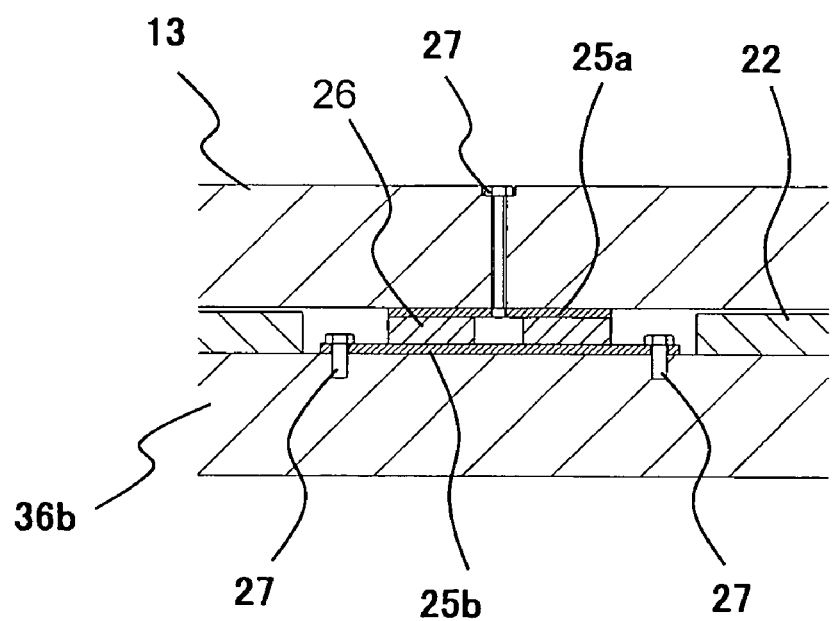
FIG. 7 represents a fourth embodiment of the present invention and shows a structure of means for supporting the vibration damper.

FIG. 7 represents a fourth embodiment of the present invention and shows a structure of means for supporting the vibration dampers 23a, 23b. More specifically, FIG. 7 corresponds to a sectional view of the vibration damper 23a taken along the line A-A in FIG. 4. In addition to the vibration damper 23a, the vibration damper 23b also has the same structure.

In FIG. 7, the vibration damper 23a has a sandwiched form in which a damper material 26 is held between two metal fittings 25a and 25b. The metal fittings 25a, 25b are fixed to the damper material 26 by bonding. Further, the metal fittings 25a, 25b are fastened respectively to the gradient magnetic field coil 13 and the cryostat 36a or 36b by bolts 27, whereby the gradient magnetic field coil 13 can be supported in a vibration isolating manner.

With such a vibration damper support structure, the height of the vibration damper 23a is just slightly higher than that of the shim tray 22. Accordingly, the dimension of the vibration damper in the direction of its height can be reduced, and the space in which the object to be examined is to be placed can be enlarged.

Meanwhile, in the case of employing the vibration dampers 23a having the same shape, the spring constant in the direction of shearing is smaller than that in the direction of compression, and a ratio of the former spring constant to the latter spring constant is, e.g., 1:10. Assuming the electromagnetic force acting on the gradient magnetic field coil 13 to be substantially equal between the vertical direction and the horizontal direction, if the spring constant in the direction of compression is optimized, the spring constant in the direction of shearing is too small and the displacement of the gradient magnetic field coil 13 in the horizontal direction is increased.

Figure 8:
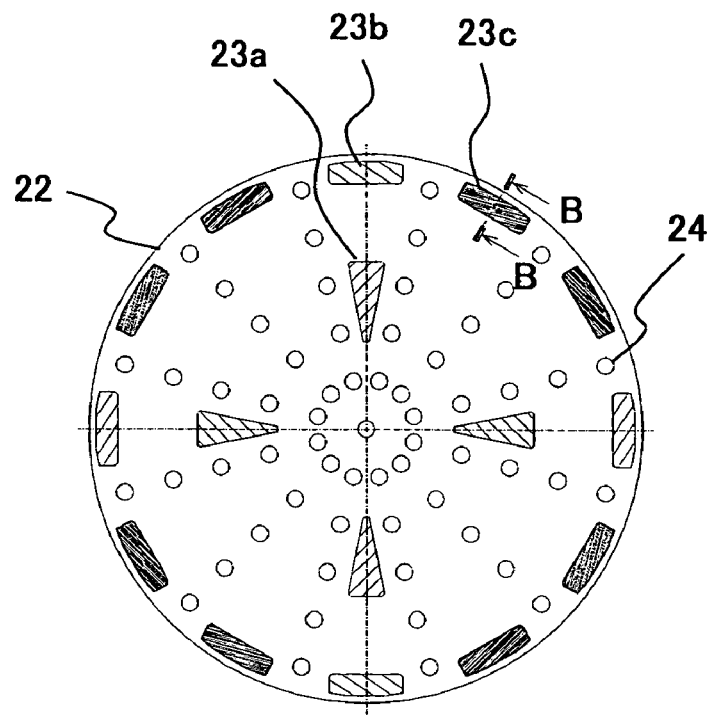
FIG. 8 is a plan view, looking from the direction of the static magnetic field, of only a shim tray and vibration dampers in an MRI apparatus according to a fifth embodiment of the present invention.

In view of the above point, in a fifth embodiment of the present invention, a vibration damper 23c for suppressing the displacement of the gradient magnetic field coil 13 in the horizontal direction is additionally attached to an outer peripheral portion of the shim tray 22 where a length in the circumferential direction can be sufficiently secured, as shown in FIG. 8.

Figure 9:
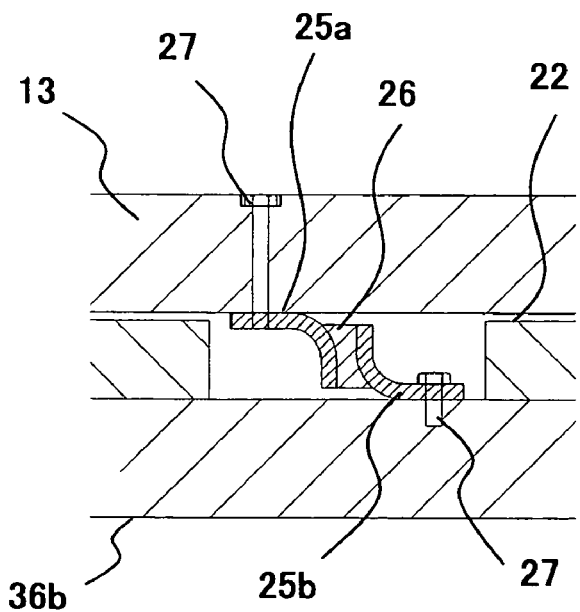
FIG. 9 is a sectional view taken along the line B-B in FIG. 8.

FIG. 9 is a sectional view taken along the line B-B in FIG. 8. In FIG. 9, a metal fitting 25a has a surface extending substantially parallel to the direction of a plane of the gradient magnetic field coil 13 and attached to the gradient magnetic field coil 13, and a surface extending substantially perpendicular to the direction of the plane of the gradient magnetic field coil 13 and supporting a damper material 26. Also, a metal fitting 25b has a surface extending substantially parallel to the direction of a plane of the lower cryostat 36b and attached to the lower cryostat 36b, and a surface extending substantially perpendicular to the direction of the plane of the lower cryostat 36b and supporting the damper material 26.

By arranging the vibration damper 23c having such a structure, the displacement of the gradient magnetic field coil 13 in the horizontal direction can be suppressed because the force acting in a direction parallel to the direction of the plane of the gradient magnetic field coil 13 is borne by the damper material 26 in the direction in which it is compressed.

Figure 10:
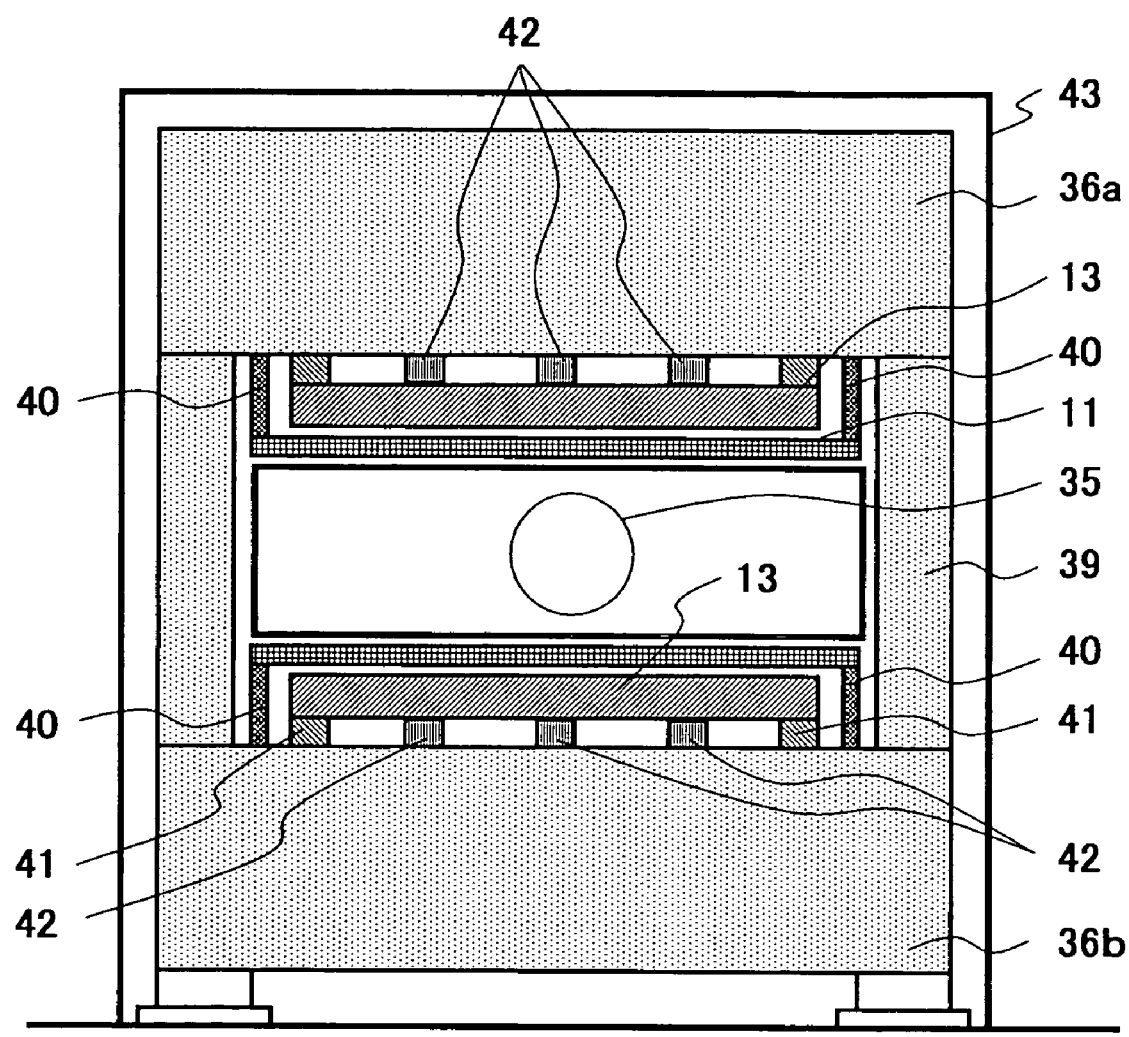
FIG. 10 is a sectional view of a gantry according to a sixth embodiment of the present invention.

FIG. 10 is a sectional view of the gantry 31 according to a sixth embodiment of the present invention. Note that the same components as those in the embodiment shown in FIG. 3 are denoted by the same reference numerals and a detailed description of those components is omitted here.

The sixth embodiment shown in FIG. 10 differs from the first embodiment shown in FIG. 3 in that the shim tray and the vibration dampers are not disposed between the gradient magnetic field coil 13 and each of the upper and lower cryostats 36a and 36b, while gradient magnetic field coil fixtures 41 and actuators 42 are disposed instead.

The actuators 42 serve to not only modify the natural frequency of fixing members depending on the mode of a method for applying the current pulse to the gradient magnetic field coil 13, but also to modify the transfer function when the vibration of the gradient magnetic field coil 13 is transmitted to the upper and lower cryostats 36a and 36b, etc., thereby causing resonance and generating noise.

In the gantry 31 having such a structure as shown in FIG. 10, the weight of the gradient magnetic field coil 13 may range from a heavy level to a light level depending on the structure actually employed. In general, however, the gradient magnetic field coil 13 is designed to be relatively heavy, i.e., in the range of about 30-400 kg, and to have relatively high rigidity.

Also, the RF coil 11 is constituted by mounting an electric element to a non-magnetic and non-conductive base member and generally has weight of about 10-50 kg. Further, the cover 43 is made of a non-metal material, such as FRP (Fiber Reinforced Plastic), with a thickness of several millimeters. In general, the cover 43 is relatively light, i.e., in the range of about 10-50 kg, and has relatively low rigidity. Thus, because various components differ in weight, etc., from each other, their vibration characteristics are also different to a large extent.

There are a plurality of transfer paths through which the vibration generated upon application of the current pulse to the gradient magnetic field coil 13 is transferred and acoustically perceived, as noise, by the object to be examined placed in the uniform magnetic space 35 of the gantry 31 and an operator standing near the gantry 31.

Figure 11:
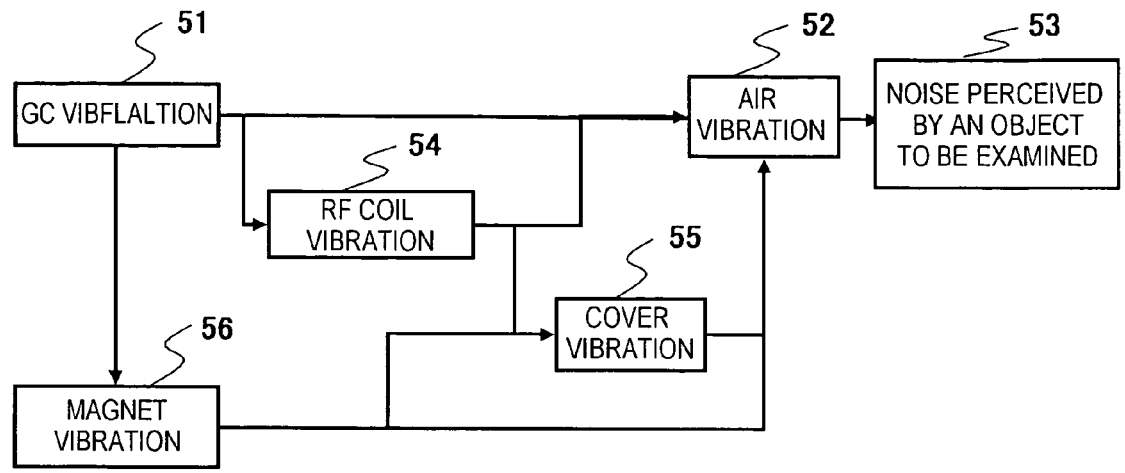
FIG. 11 is an explanatory view for explaining transfer paths of vibration of a gradient magnetic field coil.

The main transfer paths will be described below with reference to FIG. 11. First, upon application of the pulse-like current to the gradient magnetic field coil 13, the gradient magnetic field coil 13 is vibrated by the Lorentz's force (block 51). A part of that vibration is transferred as noise to the object to be examined and the operator through air (block 51→block 52→block 53). Also, another part of the vibration generated in the gradient magnetic field coil 13 is propagated through transfer paths including solid bodies, such as the RF coil 11, the magnets (cryostats), and the cover. In one of those transfer paths, for example, a part of the generated vibration is transferred to the RF coil 11 and then to air, followed by being propagated as noise to the object to be examined and the operator through air vibration (block 51→block 54→block 52→block 53).

Further, in another transfer path, the vibration transferred to the RF coil 11 is transferred to the cover 43 and is then propagated as noise to the object to be examined and the operator through air vibration (block 51→block 54 block 55→block 52→block 53). In still another transfer path, the vibration is directly transferred from the gradient magnetic field coil 13 to the magnets (cryostats) and is transferred from the magnets (cryostats) to the cover 43 and then to air, followed by being propagated as noise to the object to be examined and the operator through air vibration (block 51→block 56→block 55→block 52→block 53).

In still another transfer path, the vibration is directly transferred from the gradient magnetic field coil 13 to the magnets (cryostats) and is transferred from the magnets (cryostats) to air, followed by being propagated as noise to the object to be examined and the operator through air vibration (block 51→block 56→block 52→block 53).

On the other hand, the waveform of the current applied to the gradient magnetic field coil 13 is variously variable depending on the imaging sequence and the imaging parameters which are employed in practice. Therefore, the vibration generated in the gradient magnetic field coil 13 may have a variety of frequency components in itself depending on the imaging method.

The vibration of the gradient magnetic field coil 13 and a frequency characteristic in transfer of the vibration will be described below from the conceptual point of view.

First, FIG. 12(a) shows a frequency characteristic of a current pattern applied to the gradient magnetic field coil 13 (or a frequency characteristic of the vibration of the gradient magnetic field coil 13 itself, which is generated in accordance with the current pattern applied to the gradient magnetic field coil 13) when a certain imaging sequence is employed.

Next, (I) in FIG. 12(b) represents, as a transfer function, a transfer rate of the vibration generated in the gradient magnetic field coil 13, which is propagated through the paths described above with reference to FIG. 11 and then reaches, as noise, to the object to be examined and the operator.

Further, (I) in FIG. 12(c) represents a frequency characteristic of noise that is actually acoustically perceived by the object to be examined and the operator. The frequency characteristic in (I) of FIG. 12(c) is resulted from multiplying the characteristic in FIG. 12(a) by the characteristic in (I) of FIG. 12(b). In the case of the illustrated example, the frequency corresponding to a peak of the frequency characteristic in (I) of FIG. 12(b) is matched with or very close to the frequency corresponding to a peak of the frequency characteristic in FIG. 12(a).

Consequently, a peak of the multiplied frequency characteristic in (I) of FIG. 12(c) is increased and the noise actually acoustically perceived by the object to be examined and the operator is increased correspondingly.

In the sixth embodiment, the transfer function in (I) of FIG. 12(b) is modified as shown in (II) of FIG. 12(b) by a method and means, which will be described below, such that the peak in FIG. 12(a) and the peak in (II) of FIG. 12(b) are not matched with each other. As a result of such a modification, the frequency characteristic of the noise actually acoustically perceived by the object to be examined and the operator is given as shown in (II) of FIG. 12(c), and the height of the peak can be reduced.

Figure 12:
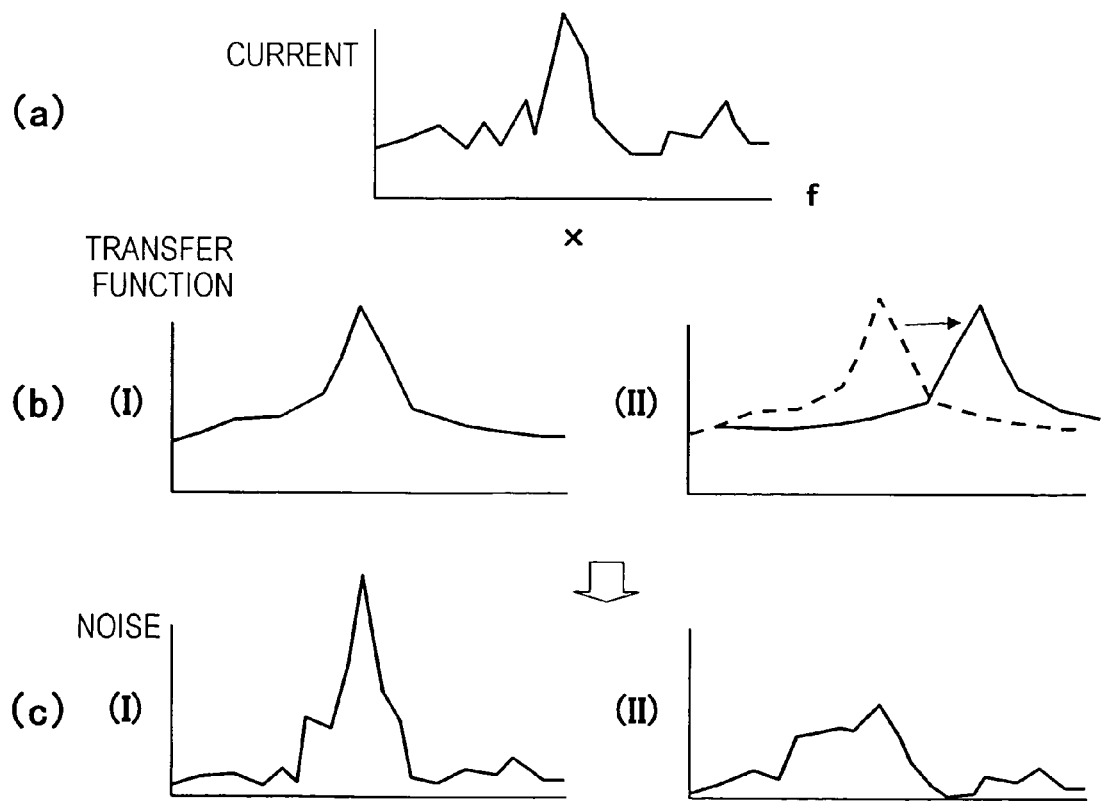
FIG. 12 is a conceptual explanatory view for explaining the vibration of the gradient magnetic field coil and a frequency characteristic in transfer of the vibration.

Thus, the noise actually acoustically perceived by the object to be examined and the operator can be held small. While the example shown in FIG. 12 represents the case having only one frequency peak, two or more frequency peaks are generally present. In such a case, the transfer function is optimized as appropriate in such a manner that the peak giving a maximum influence to the noise is reduced with priority.

The following description is made of how the transfer rate (transfer function) of the vibration, which is generated in the gradient magnetic field coil 13 and reaches as noise to the object to be examined and the operator, is modified in the sixth embodiment. To that end, a detailed arrangement for fixing the gradient magnetic field coil 13 will be described below with reference to FIG. 13.

Figure 13:
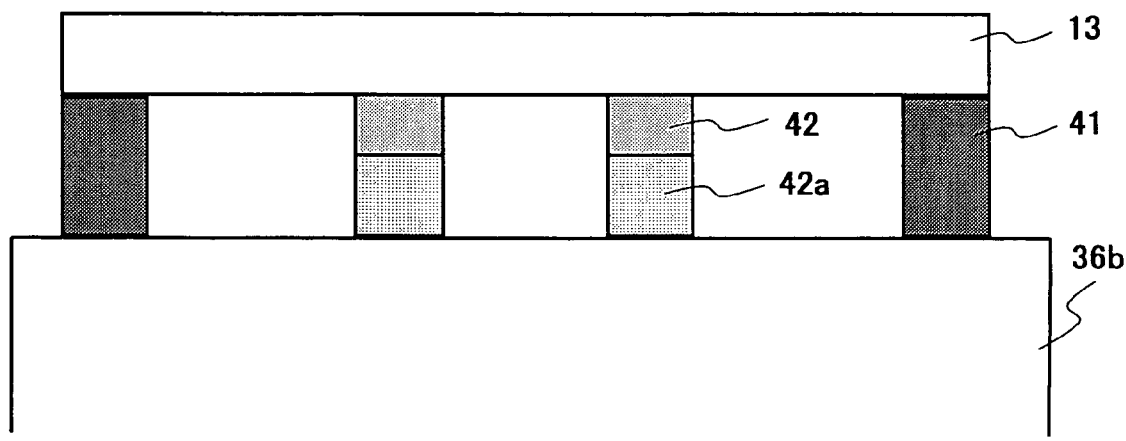
FIG. 13 is a detailed explanatory view for explaining a fixed state of the gradient magnetic field coil.

In FIG. 13, reference numeral 42a denotes a base for fixing the actuator 42 to the lower cryostat 36b. While only two gradient magnetic field coil fixtures 41 are shown in FIG. 13, the gradient magnetic field coil fixtures 41 are actually required in number sufficient for reliable support of the gradient magnetic field coil 13, and other gradient magnetic field coil fixtures 41 are omitted in FIG. 13.

The actuators 42 are arranged on the base 42a in FIG. 13, but their fore ends on the side facing the gradient magnetic field coil 13 are not in contact with the gradient magnetic field coil 13 in an ordinary state. In that case, the mode of the specific vibration generated in the gradient magnetic field coil 13, i.e., the transfer function shown in FIG. 12(b), is decided depending on the arrangement of the gradient magnetic field coil fixtures 41.

On the other hand, when any of the actuators 42 is operated to bring its fore end on the side facing the gradient magnetic field coil 13 into contact with the gradient magnetic field coil 13, the condition for fixing the gradient magnetic field coil 13 is changed. As a result, the mode of the specific vibration is changed and the transfer function is also changed correspondingly.

By computing the correlation between the contact pattern and the transfer function in advance, it is possible to make setting so that the frequency at which the transfer function is peaked (i.e., the peak frequency) and the frequency of the peak in the frequency characteristic (which is determined in advance) of the current pattern applied to the gradient magnetic field coil 13 are shifted from each other.

As a result, the generated noise can be reduced and an unpleasant feeling perceived by the object to be examined and the operator can be eliminated. Generally, when the number of points at which the gradient magnetic field coil 13 and the actuators 42 contact with each other is increased, the peak frequency is shifted toward the high frequency side. For example, by bringing the actuators 42 into contact with the gradient magnetic field coil 13, the transfer function is modified as represented by (II) in FIG. 12(b), and the frequency characteristic of the noise actually acoustically perceived by the object to be examined and the operator is given as represented by (II) in FIG. 12(c).

It is hence possible to reduce the generated noise and to eliminate an unpleasant feeling perceived by the object to be examined and the operator.

Figure 14:
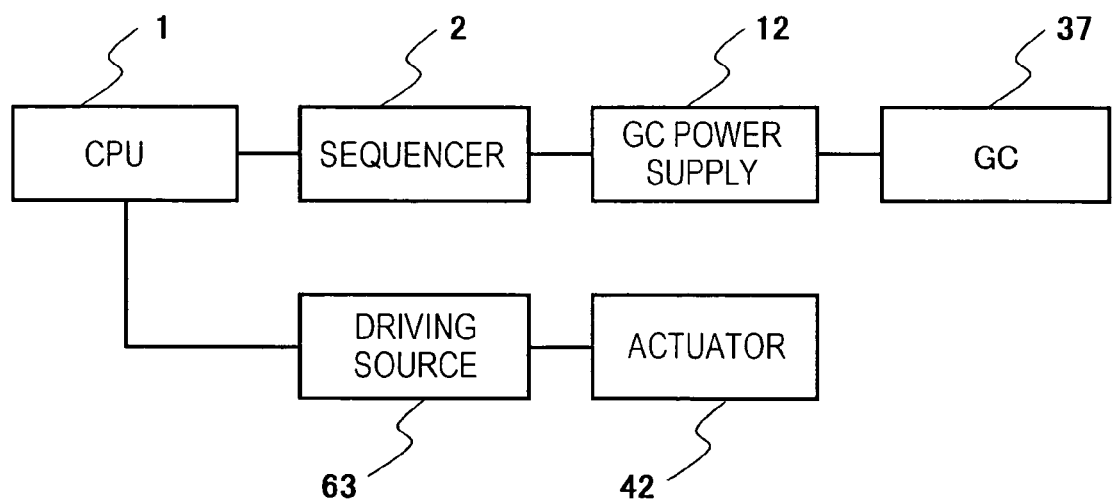
FIG. 14 is a block diagram of a control system in a sixth embodiment of the present invention.

Control for the operation of the actuator 42 will be described below with reference to FIG. 14. FIG. 14 is a block diagram of a control system in the sixth embodiment of the present invention.

In FIG. 14, commands including the imaging sequence, parameters, etc. are issued from the CPU 1, which controls the entire system, to the sequencer 2 which controls the current applied to the gradient magnetic field coil 13. In accordance with the conditions indicated by the issued commands, the CPU 1 decides which actuators are to be brought into contact with the gradient magnetic field coil 13, and supplies a control signal to a driving source 63 for driving the actuator 42 so that desired one or more of the actuators 42 are brought into contact with the gradient magnetic field coil 13.

Unlike the technique disclosed in JP,A 8-154518 in which the vibration is directly canceled, in the sixth embodiment of the present invention, the actuator 42 is statically controlled instead of being controlled at high speed during the imaging process. Accordingly, a driving circuit system, etc. are not required to operate at high speed, and they can be simplified.

Figure 15:
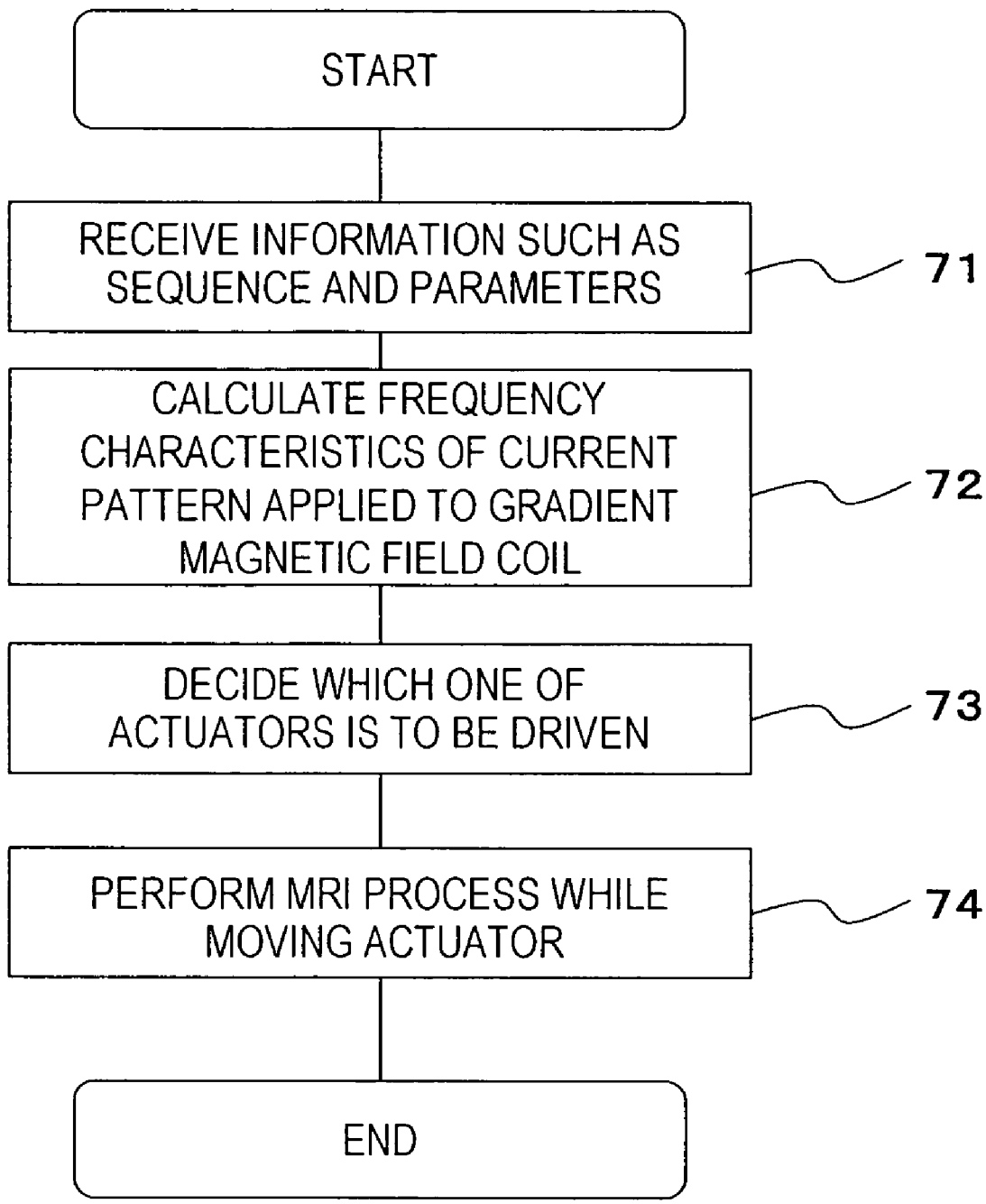
FIG. 15 is a flowchart showing an imaging operation which is performed using an MRI apparatus according to the sixth embodiment of the present invention.

The procedure in the imaging operation performed using the MRI apparatus according to the sixth embodiment will be described below with reference to a flowchart shown in FIG. 15.

First, in step 71, the operator enters information, such as the sequence and the parameters for the imaging to be performed, through the display 18, etc. Then, in step 72, the frequency characteristic of the current pattern applied to the gradient magnetic field coil 13 is computed which is required when the imaging is performed under the conditions decided from the sequence and the parameters entered in step 71.

Then, in step 73, the CPU decides which one or more of the actuators are driven to adjust the transfer function so that the vibration generated in accordance with the current pattern, which is applied to provide the frequency characteristic computed in step 72, is not acoustically perceived, as large noise, by the object to be examined and the operator.

Then, the imaging is performed while driving the relevant one or more actuators 42 as per decided in step 73.

According to the sixth embodiment of the present invention, as described above, the actuators 42 are driven to set the transfer function between the gradient magnetic field coil 13 and each of the upper and lower cryostats 36a and 36b depending on the imaging sequence so as to have a value optimum for suppressing the vibration of the gradient magnetic field coil. Therefore, the generation of the noise due to the vibration of the gradient magnetic field coil can be suppressed in a manner adaptable for each of various sequences, and image quality can be improved.

Figure 16:
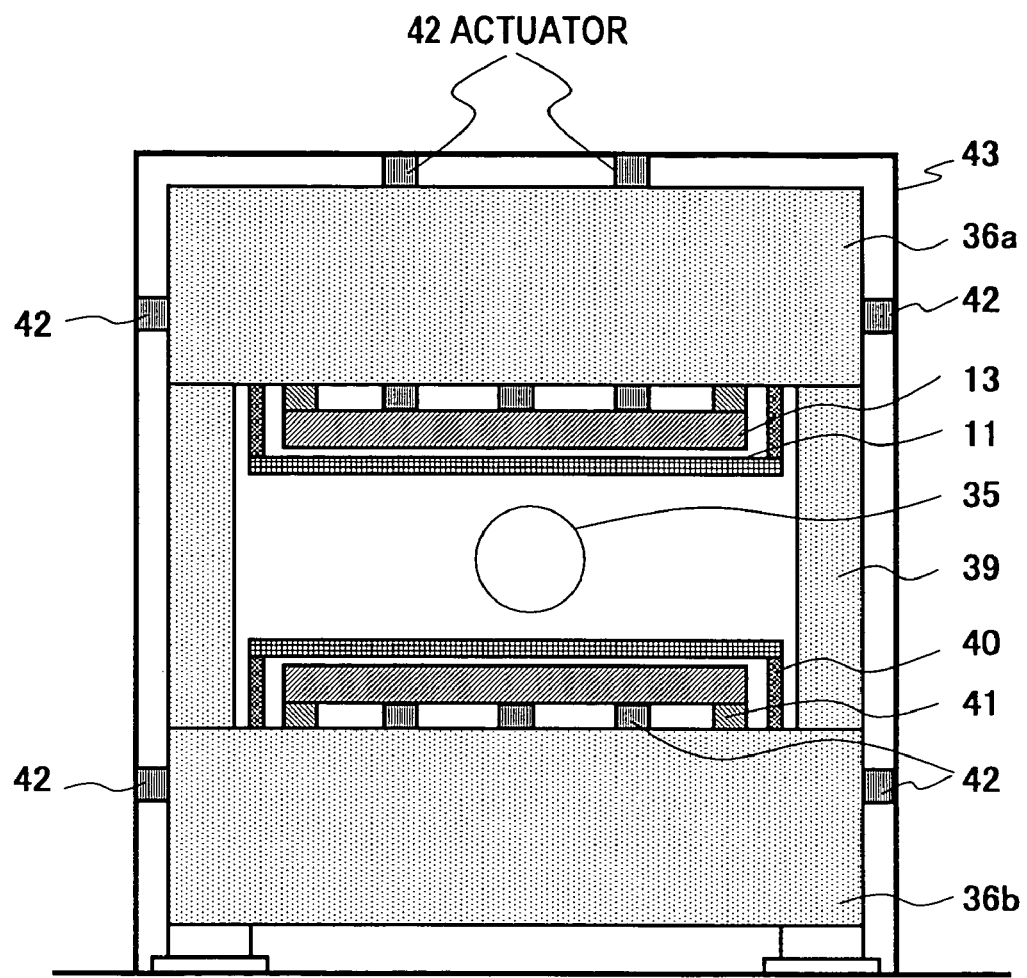
FIG. 16 is a sectional view of a gantry in a seventh embodiment of the present invention.

FIG. 16 is a sectional view of a gantry 31 in a seventh embodiment of the present invention. Note that the same components as those in the embodiment shown in FIG. 10 are denoted by the same reference numerals and a detailed description of those components is omitted here.

In the seventh embodiment shown in FIG. 16, a plurality of actuators 42 are disposed not only between the gradient magnetic field coil 13 and each of the upper and lower cryostats 36a and 36b as in the sixth embodiment shown in FIG. 10, but also between each of the upper and lower cryostats 36a and 36b and the cover 43.

In the seventh embodiment shown in FIG. 16, the transfer function between each of the upper and lower cryostats 36a and 36b and the cover 43 is changed depending on the imaging sequence so as to suppress the vibration transferred from the gradient magnetic field coil 13 to the cover 43 through the upper and lower cryostats 36a and 36b, thereby further reducing the noise.

In an eighth embodiment of the present invention, the vibration dampers 23 (23a and 23b) in the first to fifth embodiments of the present invention are employed as actuators 42 and the elasticity of one or more of the actuators 42 is changed under control so as to provide the elasticity at which the vibration can be maximally suppressed, depending on each of the various sequences.

The sixth and seventh embodiments of the present invention have been described above in connection with the case of arranging the actuators in portions where the gradient magnetic field coil 13 is fixed to each of the cryostats 36a, 36b, and in portions of the cover 43 in order to modify the transfer function. However, the other components of the gantry 31, for example, the RF coil 11 constituting the vibration transfer path shown in FIG. 11, are also vibrated with respective natural frequency characteristics.

Accordingly, the noise transferred to the object to be examined and the operator may be reduced by arranging the actuators 42 in a manner capable of contacting with those components and controlling the actuators to properly modify the frequency characteristics and the transfer functions of their vibrations.

Because each of the RF coil 11 and the cover 43 has smaller rigidity and weight than those of the gradient magnetic field coil 13, the frequency characteristics of the vibrations of the RF coil 11 and the cover 43 can be more easily modified in comparison with the case of the gradient magnetic field coil 13.

In actual control, the vibration mode of each component is controlled so that a noise level estimated from the frequency characteristic of the applied current and the respective natural vibration modes of the components constituting the system is minimized. For example, the noise generated directly with the vibration of the gradient magnetic field coil 13 can be isolated to certain extent through the RF coil 11, the cover 43, etc.

Generally, a higher effect of isolating the noise is obtained in a higher frequency range. Therefore, when the intensity of the vibration generated in the gradient magnetic field coil 13 is the same, the noise peak can be more effectively reduced by suppressing the vibration peak in a lower frequency range.

Also, human perceptivity to noise depends on frequency. Therefore, the above-described modification of the transfer function may be performed taking into account the human perceptivity as well. Further, because the generated noise differs depending on a place, design may be performed while considering the position at which noise is to be suppressed. For example, the places where the ears of the object to be examined are positioned differ depending on a body portion of the object to be examined as a target of the imaging. It is therefore preferable to select which one or more of the actuators are to be brought into contact with the corresponding components, depending on the body portion of which image is to be captured. On that occasion, a noise quieting level for the operator can also be taken into consideration.

Moreover, the actuators employed in the sixth, seventh and eighth embodiments of the present invention are switched over depending on the sequence used for the imaging, and they are not employed to directly cancel the noise unlike the technique disclosed in JP,A 8-154918. For that reason, an element incapable of being switched over between an extended state and a contracted state at high speed can also be used. For example, a shape-memory alloy, a hydraulic element, a pneumatic element, etc. are similarly usable.

The advantages of the present invention can also be obtained by arranging, e.g., rubber dampers in contact with the gradient magnetic field coil 13, and changing the temperature of the rubber dampers to change the hardness of the rubber dampers, thereby modifying the frequency characteristic of the vibration of the gradient magnetic field coil 13. The temperature of the rubber dampers can be changed by any of methods of employing a heater, changing the fluid temperature inside a pipe wound around the rubber, and utilizing a Peltier element.

The use of the rubber dampers is advantageous in that a vibration damping effect is obtained at the same time and therefore an effect of suppressing transfer of the vibration from the gradient magnetic field coil 13 to the magnet (cryostat) is also obtained. Additionally, a piezoelectric element can also be utilized as the actuator.

Figure 17:
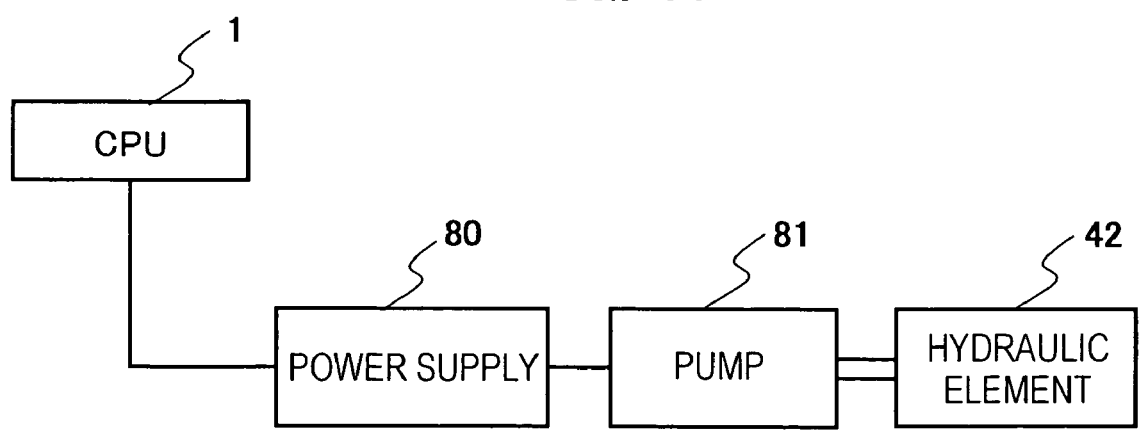
FIG. 17 is a block diagram of a driving system when a hydraulic element is used as an actuator.

FIG. 17 is a block diagram of a driving system for the actuator 42 when a hydraulic element is used as the actuator 42. In FIG. 17, the CPU 1 outputs a command to a power supply 80 so that the hydraulic element has a predetermined dimension corresponding to the sequence to be executed. In accordance with electric power supplied from the power supply 80, a pump 81 drives a cylinder of the hydraulic element serving as the actuator 42. In such a case, the hydraulic element 42 and the pump 81 are each made of a non-magnetic material in consideration of an influence on the uniformity of the magnetic field.

Figure 18:
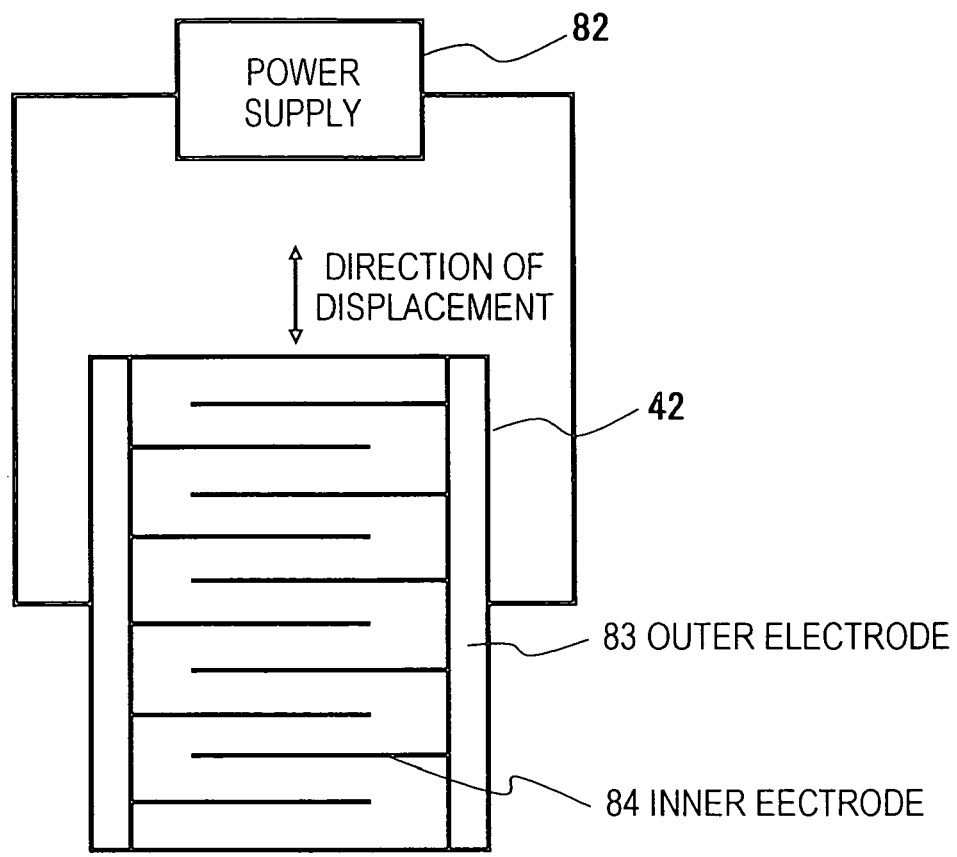
FIG. 18 is an explanatory view for explaining the case where a piezoelectric element is used as the actuator.

FIG. 18 is an explanatory view for explaining the case where a piezoelectric element is used as the actuator 42. There are piezoelectric elements having various structures, such as monomorphic and laminated structures, which are constituted on the basis of a unit element constituted by holding a piezoelectric material between two electrodes in a sandwiched form.

When the piezoelectric element is employed in the present invention, the laminated type is preferable to obtain a relatively large displacement. As shown in FIG. 18, the laminated piezoelectric element comprises an outer electrode 83, an inner electrode 84, and thin plates of piezoelectric material laminated in number of several tens to hundred. The individual thin plates of piezoelectric material are laminated such that polarization is alternately reversed in the direction of thickness of the piezoelectric element. With application of a voltage to the electrodes, the piezoelectric element is displaced in the laminating direction.

Figure 19:
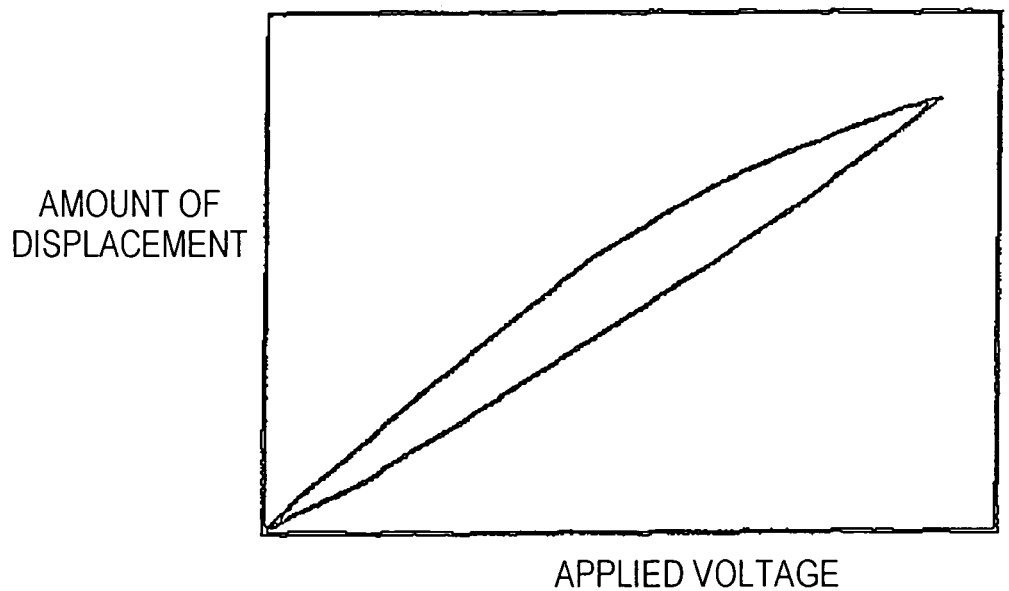
FIG. 19 is a graph for explaining the case where the piezoelectric element is used as the actuator.

In the piezoelectric element, generally, the displacement has a hysteresis characteristic with respect to the applied voltage, as shown in FIG. 19. Therefore, control is required to be performed in consideration of such a hysteresis characteristic as well.

The above description has been made in connection with means for pushing the actuator against the corresponding component in order to modify the vibration mode or the transfer function. However, another mechanism such as pulling or sandwiching the corresponding component is also usable.

Further, the sixth to eighth embodiments have been described in connection with the MRI apparatus in which the gradient magnetic field coil 13 is mounted to each of the cryostats 36a, 36b.

However, the present invention can also be applied to an MRI apparatus in which the gradient magnetic field coil 13 is mounted to, instead of the cryostat, a support stand fixed to a floor. In that case, the actuator and its base may be disposed between the support stand and the gradient magnetic field coil. Such an MRI apparatus employing the support stand has a noise suppressing effect because transfer of vibration from the gradient magnetic field coil 13 to the cryostats 36a, 36b can be cut.

Moreover, by using any of the known quieting techniques (e.g., a quieting technique based on a sequence and a vacuum shield technique) in a combined manner, the present invention can realize further quieting.

In addition, while the above embodiments have been described in connection with the case of driving the actuator to reduce the noise acoustically perceived by the object to be examined and the operator, the noise may be minimized by neither driving any actuator, nor bringing any actuator into close contact with the gradient magnetic field coil, etc. in some sequence used.

INDUSTRIAL APPLICABILITY

The present invention is not limited to the above-described embodiments and can be practiced in various modified forms without departing the gist of the invention. For example, the present invention is also applicable to a tunnel-type MRI apparatus employing a horizontal magnetic field system, i.e., an MRI apparatus in which a static magnetic field is generated in a gantry having a substantially cylindrical shape to extend along a center axis of the cylinder, and an MRI image of an object to be examined placed in an imaging space defined inside the gantry is obtained.

The invention claimed is:

1. A magnetic resonance imaging apparatus comprising
static magnetic field generating means for generating a static magnetic field in an imaging space,
gradient magnetic field generating means for generating a gradient magnetic field in the imaging space,
RF magnetic field generating means for generating an RF magnetic field to cause nuclear magnetic resonance in an object to be examined placed in the imaging space,
signal receiving means for detecting a nuclear magnetic resonance signal from said object,
signal processing means for reconstructing an image by using the detected nuclear magnetic resonance signal,
static magnetic-field non-uniformity correcting means disposed between said static magnetic field generating means and said gradient magnetic field generating means, including a plurality of static magnetic-field non-uniformity correcting members, and having a plurality of holes formed therein; and
a plurality of vibration isolating members disposed in the plurality of holes formed in said static magnetic-field non-uniformity correcting means and suppressing transfer of vibration generated in said gradient magnetic field generating means to said static magnetic field generating means.

2. The magnetic resonance imaging apparatus according to claim 1, wherein said plurality of vibration isolating members are disposed to connect said static magnetic field generating means and said gradient magnetic field generating means with each other.

3. The magnetic resonance imaging apparatus according to claim 2, wherein said static magnetic field generating part are disposed in opposed relation with the imaging space interposed therebetween, and said gradient magnetic field generating part are disposed on an inner side of said static magnetic field generating part closer to the imaging space in opposed relation with the imaging space interposed therebetween.

4. The magnetic resonance imaging apparatus according to claim 1, wherein said static magnetic field generating means are disposed in opposed relation with the imaging space interposed therebetween, and said gradient magnetic field generating means are disposed on an inner side of said static magnetic field generating means closer to the imaging space in opposed relation with the imaging space interposed therebetween.

5. The magnetic resonance imaging apparatus according to claim 4, wherein said plurality of static magnetic-field non-uniformity correcting members are arranged in said static magnetic-field non-uniformity correcting means at a density decreasing from a central area to an edge area of said static magnetic-field non-uniformity correcting means.

6. The magnetic resonance imaging apparatus according to claim 4, wherein said static magnetic-field non-uniformity correcting means has a disk-like shape, and said plurality of vibration isolating members comprise a first vibration isolating member which is disposed in a central area of said static magnetic-field non-uniformity correcting means and which has a length in the radial direction larger than a length in the circumferential direction of said static magnetic-field non-uniformity correcting means, and a second vibration isolating member which is disposed in an edge area of said static magnetic-field non-uniformity correcting means and which has a length in the circumferential direction larger than a length in the radial direction of said static magnetic-field non-uniformity correcting means.

7. The magnetic resonance imaging apparatus according to claim 6, wherein the length of said first vibration isolating member in the circumferential direction is gradually increased from a portion closer to the center of said static magnetic-field non-uniformity correcting means toward a portion closer to the edge thereof.

8. The magnetic resonance imaging apparatus according to claim 6, wherein said second vibration isolating member is disposed in the edge area of said static magnetic-field non-uniformity correcting means, having the length in the circumferential direction larger than the length in the radial direction of said static magnetic-field non-uniformity correcting means, one side surface of a portion of said second vibration isolating member having the larger length in the circumferential direction, as viewed in the radial direction of said static magnetic-field non-uniformity correcting means, being supported to said gradient magnetic field coil by first support means, the other side surface of the portion of said vibration isolating member having the larger length in the circumferential direction, as viewed in the radial direction of said static magnetic-field non-uniformity correcting means, being supported to said static magnetic field generating means by second support means.

9. The magnetic resonance imaging apparatus according to claim 1, wherein at least one of the plurality of vibration isolating members includes a vibration damper.

10. The magnetic resonance imaging apparatus according to claim 1, wherein the plurality of vibration isolating members are arranged at positions symmetric about a center of said static magnetic-field non-uniformity correcting means.

11. The magnetic resonance imaging apparatus according to claim 1, wherein spring constants of the vibration isolating members are equal to each other.

12. A magnetic resonance imaging apparatus comprising:
a static magnetic field generating part configured to generate a static magnetic field in an imagine space;
a gradient magnetic field generating part configured to generate a gradient magnetic field in the imaging space;
a RF magnetic field generating part configured to generate an RF magnetic field to cause nuclear magnetic resonance in an object to be examined placed in the imaging space;
a signal receiving part configured to detect a nuclear magnetic resonance signal from said object, and a control part configured to reconstruct an image by using the detected nuclear magnetic resonance signal and for generating the gradient magnetic field and the RF magnetic field in accordance with a plurality of pulse sequences, and
a vibration suppressing part configured to modify a frequency characteristic or a transfer characteristic of vibration caused when said gradient magnetic field generating means is vibrated,
wherein said vibration suppressing part includes actuators disposed between said static magnetic field generating part and said gradient magnetic field generating part, each of said actuators being capable of changing contact areas or contact pressures with respect to said static magnetic field generating part and said gradient magnetic field generating part, and said control part modifies the contact areas or the contact pressures of one or more of said actuators in accordance with the pulse sequence.

13. The magnetic resonance imaging apparatus according to claim 12, further comprising a cover for covering said static magnetic field generating part, said gradient magnetic field generating part, and said RF magnetic field generating part, wherein said actuators are additionally disposed between said cover and said static magnetic field generating part.

14. The magnetic resonance imaging apparatus according to claim 12, further comprising static magnetic-field non-uniformity correcting part disposed between said static magnetic field generating part and said gradient magnetic field generating part, including a plurality of static magnetic-field non-uniformity correcting members, and having a plurality of holes formed therein, wherein said actuators are disposed in said plurality of holes.

15. A magnetic resonance imaging apparatus comprising:
a static magnetic field generating means part configured to generate a static magnetic field in an imaging space;
a gradient magnetic field generating part configured to generate a gradient magnetic field in the imaging space;
a RF magnetic field generating part configured to generate an RF magnetic field to cause nuclear magnetic resonance in an object to be examined placed in the imaging space;
a signal receiving part configured to detect a nuclear magnetic resonance signal from said object;
a signal processing part configured to reconstruct an image by using the detected nuclear magnetic resonance signal;
a static magnetic-field non-uniformity correcting part including a plurality of static magnetic-field non-uniformity correcting members and a plurality of holes formed therein, said static magnetic-field non-uniformity correcting part being disposed between said static magnetic field generating part and said gradient magnetic field generating part; and
a plurality of vibration isolating members disposed in the plurality of holes formed in said static magnetic-field non-uniformity correcting part, the vibration isolating members suppressing transfer of vibration generated in said gradient magnetic field generating part to said static magnetic field generating part.

* * * * *